(12) United States Patent
Jugl et al.

(10) Patent No.: US 9,089,646 B2
(45) Date of Patent: Jul. 28, 2015

(54) HOUSING COMPONENT FOR A DRUG DELIVERY DEVICE

(75) Inventors: Michael Jugl, Frankfurt am Main (DE); Gunther Sendatzki, Frankfurt am Main (DE); Axel Teucher, Frankfurt am Main (DE); Axel Forstreuter, Frankfurt am Main (DE)

(73) Assignee: Sanofi-Aventis Deutshcland GmbH, Frankfurt am Main (DE)

( * ) Notice: Subject to any disclaimer, the term of this patent is extended or adjusted under 35 U.S.C. 154(b) by 413 days.

(21) Appl. No.: 13/389,635

(22) PCT Filed: Aug. 26, 2010

(86) PCT No.: PCT/EP2010/062431
§ 371 (c)(1),
(2), (4) Date: Jun. 27, 2012

(87) PCT Pub. No.: WO2011/023735
PCT Pub. Date: Mar. 3, 2011

(65) Prior Publication Data
US 2012/0265153 A1    Oct. 18, 2012

(30) Foreign Application Priority Data
Aug. 27, 2009  (EP) .................................. 09010975

(51) Int. Cl.
*A61M 5/315* (2006.01)
*A61M 5/24* (2006.01)
*A61M 5/31* (2006.01)

(52) U.S. Cl.
CPC ............... *A61M 5/24* (2013.01); *A61M 5/3129* (2013.01); *A61M 2005/2488* (2013.01); *A61M 2005/2492* (2013.01)

(58) Field of Classification Search
CPC ..................... A61M 5/31525–5/31563; A61M 5/31565–5/31595; A61M 2005/3125; A61M 2005/3126; A61M 2005/31533; A61M 2005/31565; A61M 2005/31576; A61M 5/14546; A61M 5/24; A61M 5/315; A61M 5/3129; A61M 2005/2488; A61M 2005/2492
USPC .......... 604/131, 181, 186–187, 218, 224, 228
See application file for complete search history.

(56) References Cited

U.S. PATENT DOCUMENTS 4,863,427 A * 9/1989 Cocchi .......................... 604/110
5,300,030 A * 4/1994 Crossman et al. ............ 604/136

(Continued)

FOREIGN PATENT DOCUMENTS

DE    102005060928 A1    6/2007
WO    9710864 A1         3/1997

(Continued)

OTHER PUBLICATIONS

Form PCT/IB/326, Notification Concerning Transmittal of International Preliminary Report on Patentability, Feb. 28, 2012.

*Primary Examiner* — Bhisma Mehta
*Assistant Examiner* — Bradley G Thomas, Jr.
(74) *Attorney, Agent, or Firm* — McDonnell Boehnen Hulbert & Berghoff LLP

(57) ABSTRACT

A housing component of a drug delivery device to accommodate a drive mechanism, wherein the drive mechanism is operable to interact with a piston of a cartridge containing a medicinal product to be dispensed by the drug delivery device. The housing component comprises at least one radially inwardly extending flange portion to be operably engaged with a piston rod of the drive mechanism, wherein that the flange portion is at least partially structurally strengthened.

12 Claims, 1 Drawing Sheet

(56) References Cited

U.S. PATENT DOCUMENTS

| | | | |
|---|---|---|---|
| 5,370,621 A * | 12/1994 | Godat et al. | 604/199 |
| 5,827,232 A | 10/1998 | Chanoch et al. | |
| 5,876,379 A * | 3/1999 | Beauvais et al. | 604/181 |
| 6,221,053 B1 * | 4/2001 | Walters et al. | 604/211 |
| 8,512,296 B2 | 8/2013 | Gabriel et al. | |
| 2002/0052578 A1 * | 5/2002 | Moller | 604/208 |
| 2007/0123829 A1 * | 5/2007 | Atterbury et al. | 604/207 |
| 2009/0048561 A1 | 2/2009 | Burren et al. | |
| 2011/0270214 A1 * | 11/2011 | Jorgensen et al. | 604/500 |

FOREIGN PATENT DOCUMENTS

| | | |
|---|---|---|
| WO | 9938554 A1 | 8/1999 |
| WO | 2007071080 A1 | 6/2007 |
| WO | 2008089886 A1 | 7/2008 |
| WO | 2008145171 A1 | 12/2008 |

\* cited by examiner

HOUSING COMPONENT FOR A DRUG DELIVERY DEVICE

CROSS REFERENCE TO RELATED APPLICATIONS

The present application is a 35 U.S.C. 371 National Application of PCT/EP2010/062431 filed Aug. 26, 2010, which claims priority to European Patent Application No. 09010975.2, filed Aug. 27, 2009, the entire contents of which are incorporated entirely herein by reference.

FIELD OF THE INVENTION

The present invention relates to drug delivery devices and in particular to pen-type injectors of the kind that provide for administration by injection of medicinal products from a multidose cartridge. In particular, the present invention relates to such pen-type injectors, where a user may set and self-administer the dose.

BACKGROUND AND PRIOR ART

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicinal product is administered on a regular or irregular basis over a short term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reducible, the device should be inexpensive to manufacture and easy to dispose. Moreover, the device should be suitable for recycling. To meet these requirements, the number of parts required to assemble the device and the number of material types the device is made from need to be kept to a minimum.

In particular for the purpose of dispensing of a dose, the drive mechanism of such drug delivery devices is adapted to exert an axially directed thrust on a piston being slidably disposed in a cartridge that contains the medicinal product. Due to the exerted thrust or pressure, the piston is displaced in distal direction, thereby expelling a well-defined dose of the medicinal product from the cartridge.

Since the drug delivery device should be light weight and cost efficient in production, most of its components, in particular the housing but as well as components of its drive mechanism are manufactured as injection molded plastic parts. Typically, during a dose dispensing procedure, at least some of the components of the drug delivery device might become subject to an at least slight elastic deformation.

Additionally, due to externally applied or internally generated mechanical forces, mechanical strain and tension may built-up during a dose dispensing procedure. Strain and/or tension, as well as elastic deformations of single or multiple components may remain in the drug delivery device also after dispensing of a dose. In practice it has turned out, that mechanical deformations and mechanical tension and/or strain may give rise to the development of so-called droplets to be observed at the tip of e.g. an injection needle or cannula being coupled to the cartridge in a fluid transferring way. It is further assumed, that due to relaxation processes or that due to vibration- or shock-induced motions of the drug delivery device, mechanical stress, tension and elastic deformations decay and vanish, e.g. due to component-inherent relaxation or inter-component vibrations.

This inevitable dissipation of elastic deformations and/or mechanical strain and/or tension may in turn lead to a further displacement of the piston into the cartridge, which, as a consequence gives rise to the unrequested development of droplets.

One approach to reduce generation of droplets comprises increasing the dimensions of components of the drug delivery device that are particularly subject to mechanical stress during dose dispensing. However, mechanically stabilizing components of the drug delivery device by simply enhancing their geometric dimensions, also the size of shrink marks, e.g. visible at the outside of the drug delivery device's housing may increase and may deteriorate the visual and haptic impression of the drug delivery device's housing. Such shrink marks are an inevitable consequence of an injection molding of plastic materials, which after injection molding is always subject to a particular shrinking process.

Objects Of The Invention

It is therefore an object of the invention, to provide a drug delivery device being less prone to mechanical and elastic deformations. It is a further object of the invention to reduce generation and built-up of droplets after dispensing of a predefined dose of a medicinal product. Further, the invention aims to provide a drug delivery device with an appealing appearance. Moreover, the drug delivery device should be inexpensive in production and should be mechanically stable and robust.

SUMMARY OF THE INVENTION

The present invention provides a housing component of a drug delivery device, which is adapted to accommodate and to receive a drive mechanism. The drive mechanism is in turn operable to interact with a piston of a cartridge that contains a medicinal product to be dispensed by the drug delivery device. In particular, the drive mechanism comprises an axially displaceable piston rod, being adapted to abut against a proximal end face of the piston for the purpose of exerting distally directed thrust to the piston, leading to a requested dispensing of a predefined dose of the medicinal product.

The housing component, which is at least partially of cylindrical geometry, comprises at least one radially inwardly extending flange portion. Said flange portion is to be operably engaged with the piston rod of the drive mechanism. Typically, said flange portion serves as axial and/or radial guiding means for the axially displaceable piston rod of the drive mechanism. In particular, the flange portion is at least partially structurally strengthened or stiffened. In this way, the stiffness, strengthness and overall stability of the housing component and that of the entire drug delivery device can be advantageously enhanced. By means of such a structurally stiffened or structurally strengthened flange portion, the housing component may become less prone to mechanical and/or elastic deformations that may otherwise arise during a dose dispensing procedure.

Due to the at least partially structurally strengthened flange portion, the built-up of elastic deformations and/or mechanical tension and/or strain in the drug delivery device and its drive mechanism can be advantageously reduced. Further, due to the structurally strengthened or stiffened housing component, post-dispensing residual elastic deformations and mechanical tension may only have a reduced impact on the generation of droplets.

According to a first preferred embodiment of the invention, the flange portion comprises a through opening, which is adapted to receive the axially displaceable piston rod. Said through opening of the radially inwardly extending or protruding flange portion matches and corresponds to the piston rod's diameter. In this way, the flange portion of the housing component serves as axial and radial guiding means for the axially displaceable piston rod.

According to another preferred embodiment of the invention, the flange portion at least partially comprises a rippled structure and/or rippled surface. By means of an uneven rippled structure or surface, the flange portion itself becomes structurally stiffened, strengthened and stabilized.

In a further preferred embodiment, the flange portion in circumferential direction comprises a corrugated structure. By making use of a corrugated or rippled shape or structure of the flange portion, a structural stiffening and strengthening can be achieved without necessarily enhancing the thickness of such flange portion.

In still another embodiment, the flange portion comprises stiffening ribs substantially extending in radial direction between an inner and an outer edge portion of the flange portion, wherein the outer edge of the flange adjoins to the inward facing side wall of the housing component.

According to a further preferred embodiment of the invention, the rippled structure of the flange portion is formed by radially extending and adjacently interconnected stiffening segments, such like stiffening ribs. Circumferentially adjacent segments are typically arranged axially staggered, which means, that the axial position of adjacently arranged stiffening segments varies alternately.

In a further preferred embodiment, the flange portion is integrally formed with the substantially cylindrical housing component. In particular, the structurally strengthened or structurally stiffened section of the flange portion is integrally formed with the cylindrical wall of the housing component. In this way, a structurally stiffening effect of the flange portion may also transfer to a corresponding structural stiffening and structural enhancement of said housing component.

In a further preferred embodiment, the housing component is manufactured as injection molded component. In particular, by means of injection molding, the cylindrical housing component and its flange portion do not have to be mutually assembled. Also, the rippled, corrugated or staggered structure of the flange portion can be simply obtained by making use of a correspondingly formed injection mold.

In another embodiment, the flange portion comprises an inner annular section and an outer annular section. The outer annular section abuts against an inner sidewall of the housing component. Typically, the outer annular section comprises a structurally strengthened or stiffened rippled structure or correspondingly rippled surface.

In a further preferred embodiment, the through opening defined by the flange portion comprises an inner thread to be engaged with an outer thread of the piston rod. In this way, the piston rod and the housing component and its flange portion respectively are threadedly engaged. By means of a rotational movement of the piston rod relative to the flange portion and relative to the housing component, the piston rod experiences a corresponding axial displacement.

In an alternative embodiment, the through opening of the flange portion comprises a non-circular geometry and/or comprises at least one radial recess or at least one radial protrusion. By means of such a design, the through opening is adapted to engage with a correspondingly shaped piston rod of e.g. non-circular geometry.

Further, the piston rod may comprise corresponding radial protrusions or recesses at its outer circumference in order to match with the structure of the through opening of the flange. By means of radial protrusions and recesses and/or by means of a non-circular geometry, the piston rod and the housing component are keyed engaged. Since by means of a keyed engagement, a rotative movement of piston rod and housing component relative to each other is essentially blocked, the at least partially structurally strengthened or stiffened flange portion may also be adapted to provide a structurally strengthened and stiffened rotational engagement of piston rod and housing component.

In a further independent aspect, the invention also relates to a drug delivery device for dispensing of a predefined dose of a medicinal product. The drug delivery device comprises a cartridge holder to receive a cartridge, wherein the cartridge is adapted to be filled with a medicinal product. The drug delivery device further comprises a drive mechanism having a piston rod, which is to be operably engaged with a piston of the cartridge in order to expel and to dispose a predefined amount of the medicinal product.

Further, the drug delivery device comprises a housing component as described above, which in turn comprises a flange portion, which is at least partially structurally strengthened according to the spirit of the present invention.

According to a further embodiment, the drug delivery device comprises a cartridge pre-filled with a medicinal product or medicament to be administered by way of injection. Hence, the drug delivery device can be designed as disposable device intended to be discarded after consumption of the medicinal product. However, the invention is by no way limited to disposable devices but can be universally realized with reusable devices, wherein an empty cartridge is to be replaced.

It will be apparent to those skilled in the art, that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

Figure 1:
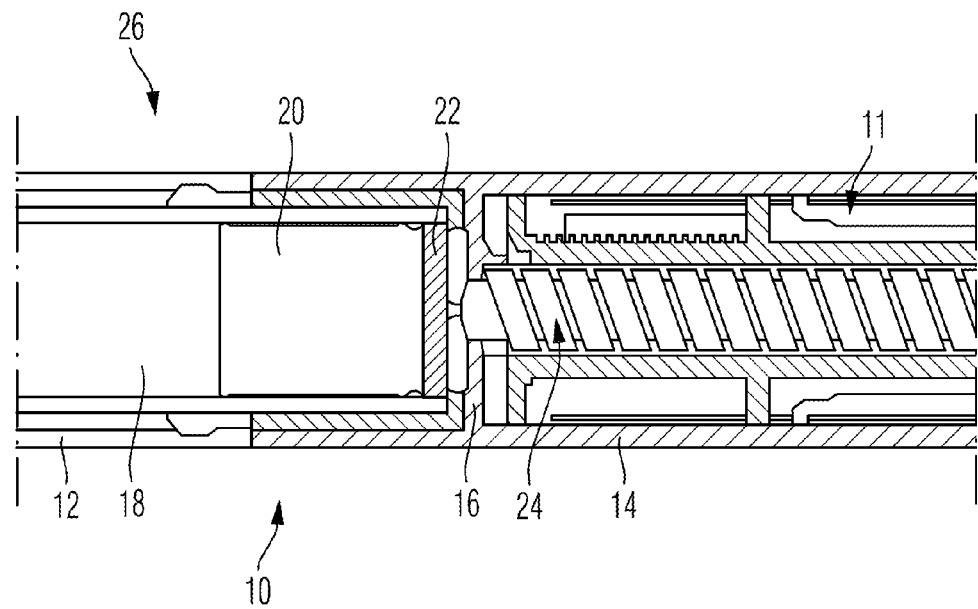
FIG. 1 schematically illustrates a drug delivery device according to the present invention in a cross-sectional side view and FIG. 2 illustrates the housing component as seen from the cartridge side in perspective illustration.

The drug delivery device 10 as illustrated in FIG. 1 comprises a cartridge holder 12 at the left hand and distal side of the drug delivery device 10 and further comprises a housing component 14 disposed at the right hand and proximal side of the illustration of the drug delivery device 10 in FIG. 1. While the cartridge holder 12 is adapted to receive a cartridge 18 filled with a medicinal product to be dispensed, the housing component 14 serves as a housing for the not further illustrated drive mechanism 11.

Irrespective of the particular function and operation of the drive mechanism 11, a piston rod 24 engaged with a pressure piece 22 is operably engaged with a piston 20 of the cartridge 18. During dispensing of a dose, the piston rod 24 is displaced in distal direction, thus exerting thrust to the piston 20. In effect, the piston 20 moves in distal direction and expels a predefined amount of the medicinal product. The cartridge holder 12 and the housing component 14 are mutually interconnected by a connection 26. The connection 26 may comprise positive or friction-locked interconnecting means, such like a threaded or clipped engagement.

Figure 2:
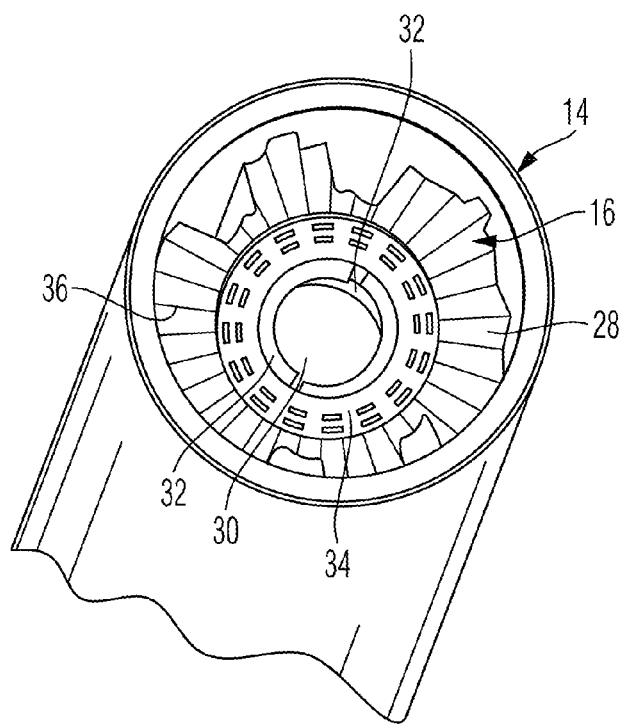

The housing component 14 further comprises a radially inwardly extending flange portion 16 as illustrated in FIG. 2. The flange portion 16 comprises a centrally located through opening 30 for receiving the piston rod 24. Also, the flange portion 16 as illustrated in FIG. 2 further comprises an inner annular section 34 as well as an outer annular section 28, wherein the outer annular section 28 is at least partially structurally stiffened or strengthened by means of a rippled structure or rippled surface as illustrated in FIG. 2.

As illustrated in FIG. 2, the outer annular section 28 comprises a series of radially extending stiffening segments 36, wherein adjacently arranged segments in circumferential direction are axially staggered. In this way, the outer annular section 28 of the flange portion 16 comprises a corrugated structure in circumferential direction.

By means of the rippled, corrugated and hence structurally strengthened and stiffened flange portion 16, the entire housing component becomes less prone to elastic deformations and storage of mechanical tension and/or strain during a dose dispensing procedure. Also, by way of providing the flange portion with a structurally enhanced structure or geometry, the overall axial wall thickness of the flange portion 16 can be kept at a moderate level, which is beneficial to counteract the development of shrink marks formed at the outer contour of the housing component 14 otherwise.

Since flange portion 16 as well as the cylindrical housing component 14 are preferably manufactured in a common plastic injection molding process, increasing of the flange portion's axial dimensions would lead to the formation of radially inwardly directed shrink marks in the outer contour of the housing component 14. By providing an alternative way to structurally enhance the housing component 14, the invention counteracts a disadvantageous generation of such shrink marks.

LIST OF REFERENCE NUMERALS 10 drug delivery device
11 drive mechanism
12 cartridge holder
14 housing
16 flange portion
18 cartridge
20 piston
22 pressure piece
24 piston rod
26 connection
28 outer annular section
30 through opening
32 inner thread
34 inner annular section
36 stiffening segment

The invention claimed is:

1. A housing component of a drug delivery device to accommodate a drive mechanism,
the drive mechanism being operable to interact with a piston of a cartridge containing a medicinal product to be dispensed by the drug delivery device, wherein the drive mechanism comprises a piston rod to abut against an end face of the piston,
wherein the tubular shaped housing component comprises at least one flange portion to be operably engaged with the piston rod, wherein the flange portion extends radially inwardly from a sidewall of the housing component, and
wherein the at least one flange portion is at least partially structurally strengthened by and comprises a rippled structure and/or a rippled surface that extends radially between an inner edge of the at least one flange portion and an outer edge of the at least one flange portion.

2. The housing component according to claim 1, wherein the at least one flange portion comprises a through opening adapted to receive the piston rod.

3. The housing component according to claim 2, wherein the through opening comprises an inner thread to be engaged with an outer thread of the piston rod.

4. The housing component according to claim 2, wherein the through opening comprises a non-circular geometry and/or at least one radial recess and/or at least one radial protrusion to engage with a corresponding non-circular geometry of the piston rod and /or to engage with at least one corresponding radial protrusion or recess disposed at an outer circumference of the piston rod.

5. The housing component according to claim 1, wherein the rippled structure and/or the rippled surface comprises a corrugated structure.

6. The housing component according to claim 1, wherein the rippled structure and/or a rippled surface comprises stiffening ribs.

7. The housing component according to claim 1, wherein the rippled structure is formed by radially extending and adjacently interconnected stiffening segments, wherein segments adjacently arranged in circumferential direction are axially staggered.

8. The housing component according to claim 1, wherein the at least one flange portion is integrally formed with the housing component.

9. The housing component according to claim 1, wherein the housing component is manufactured as injection molded component.

10. The housing component according to claim 1, wherein the at least one flange portion comprises an inner annular section and an outer annular section, wherein at least the outer annular section is structurally strengthened by the rippled structure or the rippled surface.

11. A drug delivery device for dispensing of a predefined dose of a medicinal product, comprising:
a cartridge holder to receive a cartridge containing the medicinal product;
a drive mechanism having a piston rod to be operably engaged with a piston of the cartridge,
characterized by
a housing component according to claim 1.

12. The drug delivery device according to claim 11, further comprising a cartridge filled with an injectable medicament.

* * * * *